(12) United States Patent
Yoshioka et al.

(10) Patent No.: US 6,897,064 B2
(45) Date of Patent: *May 24, 2005

(54) CELL OR TISSUE-CULTURING CARRIER, AND CULTURING METHOD

(75) Inventors: Hiroshi Yoshioka, Hadano (JP); Sunao Kubota, Kunitachi (JP); Yuichi Mori, Yokohama (JP)

(73) Assignee: Mebiol Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/483,666
(22) PCT Filed: Jul. 12, 2002
(86) PCT No.: PCT/JP02/07130

§ 371 (c)(1),
(2), (4) Date: Jan. 13, 2004

(87) PCT Pub. No.: WO03/006635

PCT Pub. Date: Jan. 23, 2003

(65) Prior Publication Data

US 2004/0203148 A1 Oct. 14, 2004

(30) Foreign Application Priority Data

Jul. 13, 2001 (JP) .......... 2001-247439

(51) Int. Cl.$^7$ ................ C12N 5/02
(52) U.S. Cl. .......... 435/397; 435/366; 435/373
(58) Field of Search .......... 435/397, 366, 435/373

(56) References Cited

U.S. PATENT DOCUMENTS

2004/0172061 A1 * 9/2004 Yoshioka et al. .......... 606/215

FOREIGN PATENT DOCUMENTS

| EP | 1 407 791 A1 | 4/2004 |
|----|----|----|
| JP | 6-141851 | 5/1994 |
| JP | 6-153928 | 6/1994 |
| JP | 6-343451 | 12/1994 |
| WO | WO 00/45868 | 8/2000 |

OTHER PUBLICATIONS

International Search Report of PCT/JP02/07130, dated Aug. 20, 2002.

International Preliminary Examination Report of PCT/JP02/07130, dated May 20, 2003.

Kubota, et al., Netsu Kagyakusei Hydrogel Polymer no Genri to Igaku Ryoiki eno Oyo, The St. Marianna medical journal. Dec. 2000, vol. 28, No. 6, pp. 729–733 (1–5).

Patent Abstract of Japan, Publication No. 06141851 A, Published on May 24, 1994, in the name of Kubota.

(Continued)

Primary Examiner—James Ketter
(74) Attorney, Agent, or Firm—Christie, Parker and Hale, LLP

(57) ABSTRACT

A cell or tissue-culturing carrier which can effectively regenerate an intended a cell or tissue, while suppressing an excessive growth of fibroblasts, and a method of culturing a cell or tissue by using the above carrier, the cell or tissue-culturing carrier wherein fibroblasts showing substantially no growing property in a gel based on the hydrogel-forming polymer, is constituted by using a hydrogel-forming polymer; an aqueous solution of which shows a thermo-reversible sol-gel transition such that it assumes a sol state at a lower temperature and assumes a gel state at a higher temperature.

8 Claims, 2 Drawing Sheets

OTHER PUBLICATIONS

Patent Abstract of Japan, Publication No. 06153928 A, Published on Jun. 3, 1994, in the name of Kubota.

Patent Abstract of Japan, Publication No. 06343451 A, Published on Dec. 20, 1994, in the name of Kubota.

Holme, K.R., et al., *Chitosan Derivatives Bearing $C_{10}$–Alkyl clycoside Branches: A Temperature–Induced Gelling Plysaccharide*, Macromolecules, vol. 24, pp 3828–3833, 1991.

N. Sarkar, *Thermal Gelation Properties of Methyl and Hydroxypropyl Methylcellose*, Journal of Applied Polymer Science, vol. 24, pp 1073–1087, 1979.

Lee, E. et al., *Transport Of Steroids In Poly(Etherurethane) And Poly (Ethylene Vinyl Acetate) Membranes*, Journal of Membrane Science, vol. 24, pp 125–143, 1985.

UEDA, *Tissue Engineering*, 1999, University of Nagoya Press.

Kawanishi, K., et al., *The Sol–Gel Transition and the Liquid–Liquid Phase Separation in Poly (vinyl chloride) Solutions*, Polymer Journal, vol. 18, No. 5, pp 411–416, 1986.

Yoshioka, H., et al., *A Synthetic Hydroget With Thermoreversible Gelation.I. Preparation And Rheological Properties*, Journal of Macromolecular Science—Pure Appl. Chem., A31(1), pp. 113–120, 1994.

Oda, et al., "Modern Industrial Chemistry" (Kindai Kyogyo Kagaku) No. 19, p. 359–360, Asakura Shoten, 1985.

Jyunpei Enami, Baiyosaibo o Mochiiru Hoho (Method of using cultured cells); edited by Meiji Saito, Saibogai Matrix (Extracellular Matrix), Medical Review Co., Ltd. (Tokyo), 1996, pp. 108–115 (English translation to follow).

Yoshikawa, et al., St. Marianna University, School of Medicine, Journal vol. 28, No. 4, pp. 161–170, 2000.

Furukawa, T., et al., *High In Vitro–In Vivo Correlation Of Drug Response Using Sponge Gel–Supported Three–Dimensional Histoculture And The MTT End Point*, Int. J. Cancer vol. 51, pp 489–498, 1992.

European Search report dated Jun. 1, 2004, for corresponding International Application EP 02 74 6025.

Partial English translation of UEDA, *Tissue Engineering*, 1999, University of Nagoya Press.

Partial English translation of ODA, et al., *Modern Industrial Chemistry* (Kindai Kyogyo Kagaku) No. 19, pp. 359–360, Asakura Shoten, 1985.

Partial English translation of Jyunpei Enami, Baiyosaibo o Mochiiru Hoho (Method of using cultured cells); edited by Meiji Saito, Saibogai Matrix (Extracellular Matrix), Medical Review Co., Ltd. (Tokyo), 1996, pp. 108–115.

Partial English translation of Yoshikawa, et al., St. Marianna University, School of Medicine, Journal vol. 28, No. 4, pp. 161–170, 2000.

English translation of Kubota, et al., *Principle of Thermo–Reversible Hydrogel Polymer And Its Application In The Medical Field*, St. Marianna medical Journal, vol. 28, No. 6, pp. 729–733, 2000.

* cited by examiner

CELL OR TISSUE-CULTURING CARRIER, AND CULTURING METHOD

CROSS-REFERENCE TO RELATED APPLICATION

This application is a National Phase Patent Application of International Application Number PCT/JP02/07130, filed on Jul. 12, 2002, which claims priority of Japanese Patent Application Number 2001-247439, filed on Jul. 13, 2001.

TECHNICAL FIELD

The present invention relates to a carrier for culturing a cell or tissue, which can preferably be used in the culture of an animal cell or tissue, and a method of culturing a cell or tissue using the carrier. More specifically, the present invention relates to a carrier for culturing a cell or tissue, which can particularly preferably be used in an in vitro three-dimensional culture (e.g., a culture for obtaining a material for tissue engineering), and a method of culturing a cell or tissue using the carrier.

A cell capable of differentiation or a tissue (including an organ) containing such a cell can be subjected to three-dimensional culture in a preferred state, and then the cell or tissue can be differentiated by using the carrier for culturing a cell or tissue according to the present invention.

BACKGROUND ART

The culture of animal cells or tissues has been widely used not only in the field of medical transplantation but also in various fields of research and development including, as typical examples, gene analysis, bioreactor for producing useful products from cells, and evaluation of biological activity of agents or drugs.

At the scene of the current medical transplantation, for example, an urgent problem is a serious shortage of donors. Whichever donors are humans or animals, securing of "living donors" would be an extremely difficult problem even in the future.

On the other hand, as an extremely dominant measure for solving the above problem regarding the donor shortage, in vitro tissue engineering (Seitaigai Soshiki Kogaku) for producing organs, tissues or apparatuses for transplantation in vitro is in the spotlight. The basic strategy of this tissue engineering is that a cell (e.g., a stem cell) is incorporated into an artificial extracellular carrier (that is also referred to as "extracellular matrix" in the field of tissue engineering) together with a physiological active substance such as a growth factor as desired, so as to regenerate a specific organ, tissue or apparatus.

It has been conventionally considered that a carrier plays only a physical and structural role in the culture of a cell or tissue, such that it constitutes the framework of a tissue or organ, determines the form of the tissue or organ, and determines the hardness, strength and flexibility of the tissue or organ. However, with the progression of developmental biology and cell biology, it has been clarified that such an extracellular carrier has various regulatory actions on activities of cells such as differentiation, growth, transferring, adhesion, signal transmittance, gene expression, hormone action, or ion channel.

Under these circumstances, in view of the expectation of functions of extracellular carriers to differentiate or propagate cells, in vitro tissue engineering has been vigorously attempted by using various types of natural or synthetic extracellular carriers such as collagen sponge which has been obtained by freeze-drying bovine collagen Type I or biodegradable polymers such as polylactic acid or polyglycolic acid (e.g., "Tissue Engineering" edited by Minoru Ueda, 1999, published by the University of Nagoya Press may be referred to).

However, since the above described existing carriers used for cell growth are solid, they have problems in that it is difficult to inoculate (or seed) or mix cells or tissues into the carriers, or in that the growth or differentiation of cells are insufficient. In addition, there are other problems in that when it is difficult to dissolve the existing carrier for cell growth or when the existing carrier is dissolved to recover regenerated tissues therefrom, the tissues regenerated in the carrier are damaged because the carrier is heated to a high temperature to dissolve itself or is subjected to enzyme treatment so as to recover the regenerated tissues.

Moreover, the most serious problem regarding the conventional carrier is that since the growth of fibroblasts occurs more vigorously than the growth or differentiation of cells that are necessary for regeneration of a tissue or organ of interest in the above carrier, the regeneration of the tissue or organ of interest becomes difficult.

DISCLOSURE OF THE INVENTION

An object of the present invention is to provide a cell or tissue-culturing carrier which functions as an artificial carrier or extracellular matrix (ECM) which has solved the above-mentioned problem encountered in the conventional cell or tissue-culturing carriers, and a method of culturing a cell or tissue by using the above carrier.

Another object of the present invention is to provide a cell or tissue-culturing carrier which can effectively regenerate an intended a cell or tissue, while suppressing an excessive growth of fibroblasts, and a method of culturing a cell or tissue by using the above carrier.

A further object of the present invention is to provide a cell or tissue-culturing carrier which exhibits substantially no antigenicity and contains substantially no known or unknown pathogenic substances, and a method of culturing a cell or tissue by using the above carrier.

A further object of the present invention is to provide a cell or tissue-culturing carrier which enables the inoculation or mixing of various cells (e.g., stem cells, precursor cells, etc.) or tissue containing these cells, and can also function as an ECM for the adhesion, differentiation or morphogenesis of various cells so as to regenerate an intended tissue or organ, and a method of culturing a cell or tissue by using the above carrier.

As a result of earnest study, the present inventors have found that when a cell or tissue-culturing carrier is constituted by using a hydrogel-forming polymer showing a thermo-reversible sol-gel transition such that it assumes a sol state at a lower temperature and assumes a gel state at a higher temperature; the growth of fibroblasts can be substantially inhibited or suppressed in the gel based on the above polymer, and that this carrier is extremely effective to achieve the above object.

The cell or tissue-culturing carrier according to the present invention is based on the above findings. More specifically, the present invention provides a cell or tissue-culturing carrier, comprising, at least a hydrogel-forming polymer; an aqueous solution of the hydrogel-forming polymer showing a thermo-reversible sol-gel transition such that it assumes a sol state at a lower temperature and assumes a gel state at a higher temperature; fibroblasts showing substantially no growing property in a gel based on the hydrogel-forming polymer.

The present invention also provides a method of culturing a cell or tissue, comprising:

providing a cell or tissue-culturing carrier comprising, at least a hydrogel-forming polymer; an aqueous solution of the hydrogel-forming polymer showing a thermo-reversible sol-gel transition such that it assumes a sol state at a lower temperature and assumes a gel state at a higher temperature; fibroblasts showing substantially no growing property in a gel based on the hydrogel-forming polymer;

adding a cell or tissue to the carrier assuming a sol state at a temperature lower than the sol-gel transition temperature thereof;

culturing the cell or tissue by using the carrier assuming a gel state at a temperature higher than the sol-gel transition temperature thereof; and recovering the cultured ell or tissue by converting again the carrier into a sol state at a temperature lower than the sol-gel transition temperature thereof.

In the cell or tissue-culturing carrier having the above-mentioned structure or constitution, the hydrogel-forming polymer may preferably includes, at least, a polymer comprising a plurality of blocks having a cloud point, and a hydrophilic block connected or combined therewith.

The sol-gel transition temperature of the above hydrogel-forming polymer may preferably be higher than 0° C. and not higher than 42° C.

The cell or tissue-culturing carrier may more preferably comprise a chemical mediator, which promotes the regeneration of a tissue or organ in a living organism.

Further, the above cell or tissue-culturing carrier can also contain a conventional extracellular matrix such as collagen and gelatin.

The aqueous solution of the above hydrogel-forming polymer may preferably exhibit a substantial water insolubility in a gel state at a higher temperature.

The above cell or tissue-culturing carrier may preferably contain at least water and the above hydrogel-forming polymer.

(Presumed Mechanism of Tissue or Organ Regeneration)

The body of an organism is generally formed from a fertilized egg (or ovum). The fertilized egg is repeatedly divided by mitosis and differentiated into different cells such as ectoderm, mesoderm or endoderm. Each of the germ layers further repeat cell division by mitosis or migration, and in the end, they become a hand, a leg, or various tissue or organs.

In a broad sense, a stem cell is a group of cells, which functions for morphogenesis in developmental processes, or for maintenance of homeostasis or germ cells in adults. An embryonic stem cell (ES cell) is a cell derived from an inner cell mass of a blastocyst, which stably grows in vitro without resulting in canceration. It can be said that the embryonic stem cell is only the stem cell capable of differentiating into any type of cells.

In a narrow sense, the stem cell is a group of cells, which functions for maintenance of homeostasis of a tissue or organ, or for the regeneration of them during wound healing, even in adults. It has been confirmed to date that stem cells are present in the hematopoietic tissue, skeletal muscle, nerve, mammary gland, epidermis, intestinal canal, sperm, etc. However, the regeneration of a cell or tissue does not occur, only in the presence of these stem cells or precursor cells. It is thought that the presence of a carrier for adhesion, differentiation or morphogenesis of stem cells or precursor cells is generally needed.

Fibroblasts are actively grown in a collagen sponge etc., which has been obtained by freeze-drying bovine collagen Type I, which is generally widely used as a carrier (or artificial extracellular matrix). Accordingly, if such a carrier is used as a cell or tissue-culturing carrier, the growth of the fibroblasts inhibits the growth or differentiation of an intended cell.

In contrast, the cell or tissue-culturing carrier according to the present invention has a function of inhibiting or suppressing the excessive growth of fibroblasts. Thus, the cell or tissue-culturing carrier according to the present invention can effectively function as an anchorage for the growth or differentiation of an intended cell, etc. That is, the cell or tissue-culturing carrier according to the present invention may play a role as an artificial extracellular matrix for adhesion, or morphogenesis of various cells (e.g., stem cells or precursor cells), thereby achieving good regeneration of a tissue or organ of a living organism.

When the cell or tissue-culturing carrier according to the present invention is formed into the state of an aqueous solution, it assumes a sol state having a fluidity at a low temperature, and therefore, the cell or tissue-culturing carrier can easily be mixed or inoculate with a cell or tissue of a living organism. Since the cell or tissue-culturing carrier according to the present invention can be converted into a gel state as such at a body temperature (37° C.), an intended cell (such as stem cell and precursor cell) can be cultured three-dimensionally in the cell or tissue-culturing carrier according to the present invention in the same manner as in a living body. Accordingly, good regeneration of a tissue or organ can be achieved by using the cell or tissue-culturing carrier according to the present invention.

For the regeneration of a tissue in a living body, there are cases where not only cells such as precursor cells, but also various chemical mediators capable of promoting the differentiation or growth of the cells, such as cell growth factor, may be required. The cell or tissue-culturing carrier according to the present invention may be converted into a gel state at a body temperature to form a three-dimensional network structure. Further, as described later, the hydrogel constituting the above carrier has a large number of hydrophobic regions or domains in the gel thereof, and the carrier can retain a chemical mediator having a strong hydrophobicity therein by hydrophobic bonding for a long period of time. Accordingly, the carrier according to the present invention can achieve a good regeneration of a tissue or organ.

When the cell or tissue-culturing carrier according to the present invention is cooled again after the culture of a cell or tissue, the carrier returns to a liquid sol state at a low temperature. Thus, the regenerated organ or tissue can be easily recovered, while they are not substantially damaged.

BEST MODE FOR CARRYING OUT THE INVENTION

Figure 1:
FIG. 1 is a photomicrograph showing an agglomeration obtained by differentiation and growth of cells which has been derived from the outside of a pancreatic duct tissue in Example 1 (on the $5^{th}$ day after the day of culture, magnification: ×100)

The present invention will be described in detail hereinbelow, with reference to figures as desired. The "part" and "%" representing a quantitative proportion or ratio are those based on mass, unless otherwise specifically noted.

(Cell or Tissue-Culturing Carrier)

The cell or tissue-culturing carrier according to the present invention comprises, at least a hydrogel-forming polymer having a sol-gel transition temperature. The cell or tissue-culturing carrier according to the present invention exhibits a thermo-reversible sol-gel transition so that it assumes a sol state at a temperature lower than the sol-gel transition temperature and it assumes a gel state at a temperature higher than the sol-gel transition temperature.

The cell or tissue-culturing carrier according to the present invention can be used not only for the purpose of the regeneration (in a narrow sense) of a cell and/or tissue, but also for the purpose of the repair of a t cell and/or tissue.
(Repair)

In the present invention, the term "repair" has a meaning such that a cell, tissue, apparatus, organ, etc., which has been lost by a certain cause (e.g., external injury, disease, surgical operation, etc.) restores its continuity by the growth of the same remaining cells or tissue thereof.
(Regeneration)

In the present invention, the term "regeneration" has a meaning such that a cell, tissue, apparatus, organ, etc., which has been lost by a certain cause (e.g., external injury, disease, surgical operation, etc.) restores its original form or shape by the growth of the same remaining cells or tissue (the term "regeneration" generally accompanies "differentiation"). In the present invention, the "regeneration" includes not only the growth of the same remaining cells or tissue, but also "repair" in which the continuity or function of the original tissue is recovered by the growth of cells or tissue which has been introduced or provided from the outside thereof.
(Hydrogel-Forming Polymer)

The hydrogel-forming polymer constituting the hydrogel according to the present invention refers to a polymer which has a crosslinking or network structure, and has a property such that it can form a hydrogel by retaining water (in the inside thereof) on the basis of such a structure. Further, the "hydrogel" refers to a gel which comprise, at least a crosslinked or network structure comprising a polymer, and water (as a dispersion liquid) supported or retained by such a structure.

The "dispersion liquid" retained in the crosslinked or network structure is not particularly limited, as long as it is a liquid comprising water as a main or major component. More specifically, the dispersion liquid may for example be either of water per se, an aqueous solution and/or water-containing liquid. The water-containing liquid may preferably contain 80 parts or more, more preferably 90 parts or more of water, based on the total 100 parts of the water-containing liquid.
(Sol-Gel Transition Temperature)

In the present invention, the terms "sol state", "gel state" and "sol-gel transition temperature" are defined in the following manner. With respect to these definitions, a paper (Polymer Journal, 18(5), 411–416 (1986)) may be referred to.

1 ml of a hydrogel in a sol state is poured into a test tube having an inside diameter of 1 cm, and is left standing for 12 hours in a water bath which is controlled at a predetermined temperature (constant temperature). Thereafter, when the test tube is turned upside down, in a case where the interface (meniscus) between the solution and air is deformed (inclusive a case wherein the solution flows out from the test tube) due to the weight of the solution per se, the above polymer solution is defined as a "sol state" at the above-mentioned predetermined temperature.

On the other hand, in a case where the interface (meniscus) between the solution and air is not deformed due to the weight of the solution per se, even when the test tube is turned upside down, the above polymer solution is defined as a "gel state" at the above-mentioned predetermined temperature.

In addition, in a case where a hydrogel in a sol state (solution) having a concentration of, e.g., about 8 mass % is used in the above-mentioned measurement, and the temperature at which the "sol state" is converted into the "gel state" is determined while gradually increasing the above "predetermined temperature" (e.g., in 1° C. increment), the thus determined transition temperature is defined as a "sol-gel transition temperature". At this time, alternatively, it is also possible to determine the above sol-gel transition temperature at which the "gel state" is converted into the "sol state" while gradually decreasing the "predetermined temperature" (e.g., in 1° C. decrement).
(Sol-Gel Transition Temperature)

In the present invention, the definition and measurement of the "sol state," "gel state," and "sol-gel transition temperature" may also be carried out as mentioned below according to the definition and method described in a publication (H. Yoshioka et al., Journal of Macromolecular Science, A31(1), 113 (1994)).

That is, the dynamic elastic modulus of a sample at an observed frequency of 1 Hz is determined by gradually shifting the temperature from a low temperature side to a high temperature side (1° C./1 min). In this measurement, the sol-gel transition temperature is defined as a temperature at which the storage elastic modulus (G', elastic term) of the sample exceeds the loss elastic modulus (G", viscous term). In general, the sol state is defined as a state in which $G''>G'$ is satisfied, and the gel state is defined as a state in which $G''<G'$ is satisfied. For the measurement of such a sol-gel transition temperature, the following measuring conditions can preferably be used.

<Measuring Conditions for Dynamic and Loss Elastic Moduli>

Measuring apparatus (trade name): Stress controlled-type rheometer (model: CSL-500, mfd. by Carri-Med Co.)

Concentration of sample solution (or dispersed liquid) (as a concentration of a "polymer compound having a sol-gel transition temperature"): 10% (by weight)

Amount of sample solution: about 0.8 g

Shape and size of cell for measurement: acrylic parallel disk (diameter: 4.0 cm), gap: 600 μm Measurement frequency: 1 Hz Stress to be applied: within linear region
(Preferred Sol-Gel Transition Temperature)

In the present invention, the above sol-gel transition temperature may preferably be higher than 0° C. and not higher than 45° C., more preferably, higher than 0° C. and not higher than 42° C. (particularly not lower than 4° C. and not higher than 40° C.) in view of the prevention of a thermal damage to cells or a tissue of a living organism.

The hydrogel material having such a preferred sol-gel transition temperature may easily be selected from specific compounds as described below, according to the above-mentioned screening method (method of measuring the sol-gel transition temperature).

In a sequence of operations wherein a tissue or organ of a living organism is regenerated by using the carrier according to the present invention, it is preferred to set the above-mentioned sol-gel transition temperature ($\underline{a}$ ° C.)

between the temperature at the time of the culturing of the cell or tissue (b° C.), and the temperature at the time of the cooling for the inoculation, mixing or recovery of the cell or tissue (c ° C.). In other words, the above-mentioned three kinds of temperatures of a ° C., b° C. and c° C. may preferably have a relationship of b>a>c. More specifically, the value of (b–a) may preferably be 1–40° C., more preferably 2–30° C. On the other hand, the value of (a–c) may preferably be 1–40° C., more preferably 2–30° C.

(Movement-Following Property of Carrier)

In view of the balance between the property of the hydrogel based on the carrier according to the present invention, and the property of the carrier for following a change in the form or shape of the tissue along with the regeneration, it is preferred that the hydrogel based on the carrier according to the present invention shows a behavior in a solid-like manner toward a higher frequency, and that the carrier shows a behavior in a liquid-like manner toward a lower frequency. More specifically, the property of the carrier for following the movements may preferably be measured according to the following method.

(Method of Measuring Movement-Following Property)

The carrier according to the present invention comprising a hydrogel-forming polymer in a sol state (i.e., at a temperature lower than the sol-gel transition temperature) is poured into a test tube having an inside diameter of 1 cm, in an amount of the carrier corresponding to a volume of 1 mL as the resultant hydrogel. Then, the above test tube is left standing for 12 hours in a water bath which is controlled at a temperature which is sufficiently higher than the sol-gel transition temperature of the carrier (e.g., a temperature which is 10° C. higher than the sol-gel transition temperature), whereby the hydrogel material is converted into a gel state.

Then, when the test tube is turned upside down, there is measured the time (T) until the interface (meniscus) between the solution and air is deformed due to the weight of the solution per se. Herein, the hydrogel will show a behavior in a liquid-like manner toward a movement having a frequency lower than $1/T$ (sec$^{-1}$), and the hydrogel will show a behavior in a solid-like manner toward a movement having a frequency higher than $1/T$ (sec$^{-1}$). In the case of the hydrogel according to the present invention, T may preferably be 1 minute to 24 hours, more preferably 5 minutes to 10 hours.

(Steady-State Flow Kinematic Viscosity)

Alternatively, the gel property of the hydrogel based on the carrier according to the present invention may preferably be determined by measuring the steady-state flow kinematic viscosity thereof. For example, the steady-state flow kinematic viscosity $\eta$ (eta) may be measured by using a creep experiment.

In the creep experiment, a predetermined shear stress is imparted to a sample, and a time-dependent change in the resultant shear strain is observed. In general, in the creep behavior of viscoelastic material, the shear rate is changed with the elapse of time in an initial stage, but thereafter shear rate becomes constant. The Steady-state flow kinematic viscosity $\eta$ is defined as the ratio of the shear stress and the shear rate at this time. This Steady-state flow kinematic viscosity can also be called Newtonian viscosity. However, it is required that the Steady-state flow kinematic viscosity is determined in the linear region wherein the viscosity little depends on the shear stress.

In a specific embodiment of the measuring method, a stress-controlled type viscoelasticity-measuring apparatus (model: CSL-500, mfd. by Carri-Med Co., USA) is used as the measuring apparatus, and an acrylic disk (having a diameter of 4 cm) is used as the measuring device, and the resultant creep behavior (delay curve) is measured for at least five minutes with respect to a sample having a thickness of 600 $\mu$m. The sampling time is once per one second for the initial 100 seconds, and once per ten seconds for subsequent period.

When the shear stress (stress) to be applied to the sample is determined, the shear stress should be set to a minimum value such that a displacement angle of $2\times10^{-3}$ rad or more is detected, when such a shear stress is loaded for ten seconds counted from the initiation of the measurement. When the resultant data is analyzed, at least 20 or more measured values are adopted with respect to the measurement after five minutes. The hydrogel based on the carrier according to the present invention may preferably have an $\eta$ of $5\times10^3$–$5\times10^6$ Pa·sec, more preferably $8\times10^3$–$2\times10^6$ Pa·sec, particularly, not less than $1\times10^4$ Pa·sec and not more than $1\times10^6$ Pa·sec, at a temperature which is about 10° C. higher than the sol-gel transition temperature.

When the above $\eta$ is less than $5\times10^3$ Pa·sec, the fluidity becomes relatively high even in a short-time observation, and the three-dimensional supporting of the cell or tissue by the gel is liable to be insufficient, and therefore, the hydrogel is less liable to function as a carrier in some cases. On the other hand, when $\eta$ exceeds $5\times10^6$ Pa·sec, the tendency that the gel shows little fluidity even in a long-time observation is strengthened, and difficulty in the movement-following property of a tissue of a living organism is increased. In addition, when $\eta$ exceeds $5\times10^6$ Pa·sec, the possibility that the gel shows a fragility is strengthened, and the tendency of brittle fracture that, after a slight pure elastic deformation, the gel is easily destroyed at a stroke is strengthened.

(Dynamic Elastic Modulus)

Alternatively, the gel property of the hydrogel based on the carrier according to the present invention may preferably be determined by measuring the dynamic elastic modulus thereof. Provided that when a strain $\gamma(t)=\gamma_0 \cos \omega t$ (t is time) having an amplitude $\gamma_0$, number of vibrations of $\omega/2\pi$ to the gel, a stress $\sigma(t)=\sigma_0 \cos(\omega t+\delta)$ having a constant stress of $\sigma_0$ and a phase difference of $\delta$ is obtained. When $|G|=\sigma_0/\gamma_0$, the ratio (G"/G') between the dynamic elastic modulus $G'(\omega)=|G|\cos\delta$ and the loss elastic modulus $G"(\omega)=|G|\sin\delta$ is an indicator showing the degree of gel property.

The hydrogel based on the carrier according to the present invention behaves as a solid toward a stress of $\omega/2\pi=1$ Hz (corresponding to a fast movement), and behaves as a liquid toward a stress of $\omega/2\pi=10^{-4}$ Hz (corresponding to a slow movement). More specifically, the hydrogel based on the carrier according to the present invention may preferably show the following property (with respect to the details of the method of measuring elastic modulus, e.g., literature: "Modern Industrial Chemistry" (Kindai Kyogyo Kagaku) No. 19, edited by Ryohei Oda, et al., Page 359, published by Asakura Shoten, 1985 may be referred to).

In the case of $\omega/2\pi=1$ Hz (number of vibrations at which the gel behaves as a solid), the ratio $(G"/G')_s=(\tan \delta)_s$ may preferably be less than 1 (preferably 0.8 or less, particularly, 0.5 or less).

In the case of $\omega/2\pi=10^{-4}$ Hz (number of vibrations at which the gel behaves as a liquid), the ratio $(G"/G')_L=(\tan \delta)_L$ may preferably be 1 or more (preferably 1.5 or more, particularly, 2 or more).

The ratio $\{(\tan \delta)_s/(\tan \delta)_L\}$ between the above $(\tan \delta)_s$ and $(\tan \delta)_L$ may preferably be less than 1 (mire preferably 0.8 or less, particularly, 0.5 or less).

<Measurement Conditions>

Concentration of hydrogel-forming polymer (carrier): about 8 mass %

Temperature: a temperature which is about 10° C. higher than the sol-gel transition temperature of the carrier Measuring apparatus: Stress controlled-type rheometer (model: CSL-500, mfd. by Carri-Med Co., USA)

(Control of Residual Property in Living Body)

It is possible to arbitrarily control the residual (or remaining) property of the hydrogel according to the present invention in a living body (in the abdominal cavity, the subcutis, etc.), as desired. The hydrogel according to the present invention is mainly intended to be used in vitro. However, depending on its usage (for example, when a tissue which has been grown by using the hydrogel according to the present invention are returned into a living body), there are cases where the control of the in vivo remaining property of the hydrogel is preferred.

If the sol-gel transition temperature of the hydrogel according to the present invention is decreased, the hydrogel tends to remain in a living body for a long period of time. In contrast, if the sol-gel transition temperature of the hydrogel according to the present invention is increased, the hydrogel tends to rapidly disappear in a living body. Further, if the concentration of the hydrogel-forming polymer in the hydrogel is increased, the hydrogel tends to remain in a living body for a long period of time. If the concentration of the hydrogel-forming polymer in the hydrogel is decreased, the hydrogel tends to rapidly disappear in a living body.

In the hydrogel according to the present invention, if the sol-gel transition temperature of the hydrogel according to the present invention is decreased, the storage elastic modulus (G') of the hydrogel at a living body temperature (37° C.) is increased. Further, if the concentration of the hydrogel-forming polymer in the hydrogel is increased, the storage elastic modulus (G') of the hydrogel at a living body temperature (37° C.) is increased. That is, in order to control the residual property of the hydrogel in a living body, G' at 37° C. may be controlled.

To measure the value of G', the following measuring conditions can preferably be used.

<Conditions for Measurement of Dynamic and Loss Elastic Moduli>

Measuring apparatus (trade name): Controlled stress rheometer CSL 500 mfd. by Carri-Med Co.

Amount of sample solution: about 0.8 g

Shape and size of cell for measurement: acryl parallel disk (diameter: 4.0 cm), gap: 600 $\mu$m Measurement frequency: 1 Hz Stress to be applied: within linear region The relationship between the residual period for the hydrogel according to the present invention in a living body, and G' is also dependent on the site or portion therefor in a living body. However, according to the findings of the present inventors, for example, the relationship between the residual period for the hydrogel in the abdominal cavity and G' at an observation frequency of 1 Hz is as follows.

That is, the desired range of G' for providing the hydrogel disappearance of 3 days or less is 10 to 500 Pa. The desired range of G' for providing the hydrogel disappearance of the hydrogel remaining for a period of not less than 3 days and not more than 14 days is 200 to 1,500 Pa. The desired range of G' for providing the hydrogel disappearance of the hydrogel remaining for a period of more than 14 days is 400 to 10,000 Pa.

(Fibroblast Growing Property)

In the present invention, fibroblasts exhibit substantially no growth in the hydrogel based on the hydrogel-forming polymer constituting the carrier. In general, when fibroblasts are subjected to monolayer culture on a dish (plate) for cell culture or are cultured in a collagen gel, the fibroblasts are significantly grown so as to provide a change thereof into an arboroid form peculiar to the fibroblasts (e.g., Jyunpei Enami, Baiyosaibo o Mochiiru Hoho (Method of using cultured cells); edited by Meiji Saito, Saibogai Matrix (Extracellular Matrix), published by Medical Review Co., Ltd. (Tokyo), 1996, pp. 108–115, may be referred to) On the contrary, in the hydrogel according to the present invention, fibroblasts maintain a spherical form thereof and they exhibit substantially no growth.

(Presumed Mechanism for Inhibition of Growth of Fibroblasts)

The mechanism of the fibroblast growth inhibition in the cell or tissue-culturing carrier according to the present invention is not necessarily clear, the mechanism may be presumed in the following manner according to the findings of the present inventors.

That is, a fibroblast has a property that it recognizes a monolayer culture, i.e., the surface of a supporting medium, and adheres thereto, whereby it actively grows two-dimensionally. A collagen gel has a structure such that a large number of collage molecules (molecular weight: 300,000) with a length of 300 nm and a diameter of 1.5 nm are aggregated and are regularly arranged, and that they become collagen fibril and form a network structure in water. Since this network structure is greater than the wavelength of visible radiation (400 nm or more), the collagen gel generally looks clouded or turbid. The collagen gel is used as a carrier for a three-dimensional culture. It is presumed that since a fibroblast recognizes the surface of a thick collagen fibril as a supporting medium and adheres thereto, this cell significantly grows two-dimensionally in the collagen gel.

In contrast, in the cell or tissue-culturing carrier according to the present invention, since the hydrogel is constituted such that a hydrogel-forming polymer in a molecular state forms a three-dimensional network structure, the heterogeneity of the structure is smaller than that of the wavelength of visible radiation, and it has a relatively high transparency. Accordingly, it is presumed that fibroblasts do not clearly recognize the surface of a two-dimensional supporting medium in the material according to the present invention, and that as a result, an excessive growth of fibroblasts is inhibited in the material according to the present invention.

(Evaluation of Growing Property of Fibroblasts)

The growth of fibroblasts can be evaluated by the following method (with respect to the details thereof of this method, e.g., Tsuyoshi Yoshikawa, Ken Tsukikawa, St. Marianna University, School of Medicine, Journal Vol. 28, No. 4, pp. 161–170 (2000) may be referred to).

A hydrogel-forming polymer constituting the cell or tissue-culturing carrier according to the present invention is dissolved in a culture solution such as RPMI-1640 (Life Technologies, N.Y., USA) at a low temperature (for example, 4° C.), under stirring. Thereafter, normal human lung fibroblasts (NHLF, mfd. by Takara Shuzo Co., Ltd.) are dispersed in the above solution, so that the cell density is set to $6 \times 10^4$ cells/mL. 0.2 mL of the resultant NHLF dispersion is poured into each well of a 24-well plate (material: plastic; the size of a well: about 15 mm long, 15 mm wide, and 20 mm depth; e.g., a commercial item such as Multiwell (trade name) mfd. by Becton-Dickinson), and then is formed into a gel state at 37° C. Thereafter, 0.4 mL of culture solution is added thereto, and then is cultured at 37° C. under 5% $CO_2$, atmospheric pressure. The growth of fibroblasts is observed along with the elapse of time (e.g., on the 0th, 1st, 3rd and 7th days after the day of culture), by using a phase-contrast microscope.

(Growth Rate of Fibroblasts)

Further, the growth rate of fibroblasts can be determined in the culturing period by the following method using an enzyme activity.

For example, a 24-well plate as described above is used, and fibroblasts are cultured thereby for a certain period of time in the cell or tissue-culturing carrier according to the present invention, and the temperature of the carrier is decreased to a temperature lower than the sol-gel transition temperature thereof (e.g., a temperature which is 10° C. lower than the sol-gel transition temperature), so as to dissolve the carrier. Thereafter, 50 µl of a WST-8 reagent (mfd. by Dojin Kagaku (Dojindo Laboratories)) as a reagent for determining the activity of succinate dehydrogenase is added to each of the wells.

The thus prepared 24-well plate is subjected to a reaction at a temperature which is lower than the sol-gel transition temperature (e.g., a temperature which is 10° C. lower than the sol-gel transition temperature, for example, at 10° C.) for 10 hours, and it is then retained at about 4° C. for 1 hour, so that a completely homogenous aqueous solution is prepared. 200 µl of each of the thus obtained aqueous solution is poured into each well of a 96-well plate. The resultant absorbance (OD (450)) is measured at 450 nm (reference wavelength: 620 nm) by using a chromatometer for microplates. It has been confirmed that there is a proportional relationship between the thus obtained OD (450) and the number of vital cells (e.g., Furukawa T. et al., "High in vitro-in vitro correlation of drug response using sponge gel-supported three-dimensional histoculture and MTT end point," Int. J. Cancer 51: 489, 1992 may be referred to). That is, the growth rate of fibroblasts is obtained as a ratio ($OD_L/OD_f$) between the absorbance at the beginning of the culture $OD_f=(OD (450))$ and the absorbance after the culture $OD_L=(OD (450))$.

In the present invention, the growth rate of fibroblasts $P_F=(OD_L/OD_f)$ which has been obtained after the culture thereof at 37° C. for 3 days may preferably be within the range of not lower than 70% and not higher than 200%. The growth rate ($OD_L/OD_f$) is more preferably within the range of not lower than 80% and not higher than 150%, and particularly preferably within the range not lower than 90% and not higher than 120%.

(Relative Growing Property of Fibroblasts)

In the present invention, it is preferred that in gel based on the hydrogel-forming polymer, the growth of intended cells (other than fibroblasts) is not inhibited relatively, while the growth of fibroblasts is inhibited. More specifically, the ratio ($P_T/P_F$) between the growth rate of the intended cells $P_T$ and the growth rate of the above fibroblasts $P_F$ may preferably be 1.1 or more. The ratio ($P_T/P_F$) may more preferably be 1.5 or more, and particularly preferably 2 or more. The growth rate $P_T$ of the intended cells can be determined as follows.

The growth rate of cells other than fibroblasts $P_T$ may be determined in the same manner as in the above determination of the growth rate of fibroblasts $P_F$ except that human colon cancer cells (SW-948, trade name: Colonic Adenoma Cell Lines, mfd. by Dainippon Pharmaceutical Co., Ltd.) are used instead of normal human lung fibroblasts (NHLF) used in the above determination of the fibroblast growth rate $P_F$. (The growth rates $P_T$ and $P_F$ are determined under the same conditions).

The ratio ($P_T/P_F$) is obtained from the values of the growth rates $P_T$ and $P_F$ as determined above.

(Hydrogel-Forming Polymer)

The hydrogel-forming polymer usable for the carrier according to the present invention is not particularly limited, as long as the polymer exhibits the above-mentioned thermo-reversible sol-gel transition (that is, as long as it has a sol-gel transition temperature). It is preferable to achieve a preferred sol-gel transition temperature by adjusting the cloud point of a plurality of blocks having a cloud point and the cloud point of a hydrophilic block in the hydrogel-forming polymer, the compositions, hydrophobicity or hydrophilicity of both types of blocks, and/or their molecular weights, in view of easy exhibition of a preferred sol-gel transition at a physiological temperature (about 0° C. to 42° C.).

As specific examples of the polymer such that an aqueous solution thereof has a sol-gel transition temperature, and it reversibly assumes a sol state at a temperature lower than the sol-gel transition temperature., there have been known, e.g., polyalkylene-oxide block copolymer represented by block copolymers comprising polypropylene oxide portions and polyethylene oxide portions; etherified (or ether group-containing) celluloses such as methyl cellulose and hydroxypropyl cellulose; chitosan derivatives (K. R. Holme. et al. Macromolecules, 24, 3828 (1991)), etc.

In addition, there has been developed a gel utilizing Pluronic F-127 (trade name, mfd. by BASF Wyandotte Chemical Co.) comprising a polypropylene oxide portion and polyethylene oxide portions bonded to the both terminals thereof.

It is known that a high-concentration aqueous solution of the above Pluronic F-127 is converted into a hydrogel at a temperature of not lower than about 20° C., is converted into an aqueous solution at a temperature lower than this temperature. However, this material can assume a gel state only at a high concentration of not lower than about 20 wt. %. In addition, even when such a gel having a high concentration of not lower than about 20 wt. % is maintained at a temperature higher than the gel-forming temperature, the gel is dissolved when water is further added thereto. In addition, since the molecular weight of the Pluronic F-127 is relatively low, and it shows an extremely high osmotic pressure at a high concentration of not less than about 20 wt. %, and simultaneously the Pluronic F-127 may easily permeate the cell membranes, whereby the Pluronic F-127 can adversely affect cells and microorganisms.

On the other hand, in the case of an etherified cellulose represented by methyl cellulose, hydroxypropyl cellulose, etc., the sol-gel transition temperature thereof is as high as about 45° C. or higher (N. Sarkar, J. Appl. Polym. Science, 24, 1073, (1979)). Accordingly, such an etherified cellulose is less liable to form a gel at body temperature (about 38° C.), and therefore it is difficult to use such a material for the above-mentioned purposes according to the present invention.

As described above, when a conventional polymer having a sol-gel transition temperature in an aqueous solution thereof, and reversibly assuming a sol state at a temperature lower than the above transition temperature is simply used, the following problems are posed:

(1) If the polymer is once converted into a gel state at a temperature higher than the sol-gel transition temperature, the resultant gel is dissolved when water is further added thereto;

(2) The polymer has a sol-gel transition temperature higher than the body temperature (in the neighborhood of 38° C.), and therefore the polymer assumes a sol state in the interior of a living body;

(3) It is necessary to increase the concentration of the polymer in an aqueous solution thereof to an extremely high value, in order to convert the polymer into a gel state; etc.

On the other hand, according to the present inventor's investigation, it has been found that the above problem can be solved by constituting the carrier according to the present invention by use of a polymer having a sol-gel transition temperature of higher than 0° C. and not higher than 42° C. (e.g., a polymer which comprises a plurality of polymer chains having a cloud point, and a hydrophilic polymer chain block which has been bonded thereto; and an aqueous solution of which has a sol-gel transition temperature, and reversibly assumes a sol state at a temperature lower than the sol-gel transition temperature).

(Preferred Hydrogel-Forming Polymers)

The hydrogel-forming polymer preferably usable as the carrier according to the present invention may preferably comprise a combination of plural hydrophobic blocks having a cloud point, and a hydrophilic block bonded thereto. The presence of the hydrophilic block is preferred in view of the provision of the water-solubility of the hydrogel material at a temperature lower than the sol-gel transition temperature. The presence of the plural hydrophobic block having a cloud point is preferred in view of the conversion of the hydrogel material into a gel state at a temperature higher than the sol-gel transition temperature. In other words, the blocks having a cloud point become water-soluble at a temperature lower than the cloud point, and are converted into a water-insoluble state at a temperature higher than the cloud point, and therefore these blocks function as crosslinking points constituted by hydrophobic bonds for forming a gel at a temperature higher than the cloud point. That is, the cloud point based on the hydrophobic bonds corresponds to the above-mentioned sol-gel transition temperature of the hydrogel.

However, it is not always necessary that the cloud point corresponds to the sol-gel transition temperature. This is because the cloud point of the above-mentioned "blocks having a cloud point" is generally influenced by the bonding between the hydrophilic block and the blocks having a cloud point.

The hydrogel to be use in the present invention utilizes a property of hydrophobic bonds such that they are not only strengthened along with an increase in temperature, but also the change in the hydrophobic bond strength is reversible with respect to the temperature. In view of the formation of plural crosslinking points in one molecule, and the formation of a gel having a good stability, the hydrogel-forming polymer may preferably have a plurality of "blocks having cloud point".

On the other hand, as described above, the hydrophilic block in the hydrogel-forming polymer has a function of causing the hydrogel-forming polymer to be changed into a water-soluble state at a temperature lower than sol-gel transition temperature. The hydrophilic block also has a function of providing the state of an aqueous (or water-containing) gel, while preventing the aggregation and precipitation of the hydrogel material due to an excess increase in the hydrophobic binding force at a temperature higher than the transition temperature.

(Plural Blocks having Cloud Point)

The plural block having a cloud point may preferably comprise a polymer block which shows a negative solubility-temperature coefficient with respect to water. More specifically, such a polymer may preferably be one selected from the group consisting of: polypropylene oxide, copolymers comprising propylene oxide and another alkylene oxide, poly N-substituted acrylamide derivatives, poly N-substituted methacrylamide derivatives, copolymers comprising an N-substituted acrylamide derivative and an N-substituted methacrylamide derivative, polyvinyl methyl ether, and partially-acetylated product of polyvinyl alcohol.

In order to prepare a block having a cloud point which is decomposed and absorbed in a living body, it is effective to use a polypeptide comprising a hydrophobic amino acid and a hydrophilic amino acid, as the block having a cloud point. Alternatively, a polyester-type biodegradable polymer such as polylactic acid or polyglycolic acid can also be used as a block having a cloud point which is decomposed and absorbed in a living body.

It is preferred that the above polymer (block having a cloud point) has a cloud point of higher than 4° C. and not higher than 40° C., in view of the provision of a polymer (compound comprising a plurality of blocks having a cloud point, and a hydrophilic block bonded thereto) to be used in the present invention having a sol-gel transition temperature of higher than 4° C. and not higher than 40° C.

It is possible to measure the cloud point, e.g., by the following method. That is, an about 1 wt. %-aqueous solution of the above polymer (block having a cloud point) is cooled to be converted into a transparent homogeneous solution, and thereafter the temperature of the solution is gradually increased (temperature increasing rate: about 1° C./min.), and the point at which the solution first shows a cloudy appearance is defined as the cloud point.

Specific examples of the poly N-substituted acrylamide derivatives and poly N-substituted methacrylamide derivatives are described below.

Poly-N-acryloyl piperidine
Poly-N-n-propyl methacrylamide
Poly-N-isopropyl acrylamide
Poly-N,N-diethyl acrylamide
Poly-N-isopropyl methacrylamide
Poly-N-cyclopropyl acrylamide
Poly-N-acryloyl pyrrolidine
Poly-N,N-ethyl methyl acrylamide
Poly-N-cyclopropyl methacrylamide
Poly-N-ethyl acrylamide The above polymer may be either a homopolymer or a copolymer comprising a monomer constituting the above polymer and "another monomer". The "another monomer" to be used for such a purpose may be either a hydrophilic monomer, or a hydrophobic monomer. In general, when copolymerization with a hydrophilic monomer is conducted, the resultant cloud point may be increased. On the other hand, when copolymerization with a hydrophobic monomer is conducted, the resultant cloud point may be decreased. Accordingly, a polymer having a desired cloud point (e.g., a cloud point of higher than 4° C. and not higher than 40° C.) may also be obtained by selecting such a monomer to be used for the copolymerization.

(Hydrophilic Monomer)

Specific examples of the above hydrophilic monomer may include: N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinyl sulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. However, the hydrophilic monomer to be usable in the present invention is not restricted to these specific examples.

(Hydrophobic Monomer)

On the other hand, specific examples of the above hydrophobic monomer may include: acrylate derivatives and methacrylate derivatives such as ethyl acrylate, methyl methacrylate, and glycidyl methacrylate; N-substituted alkyl methacrylamide derivatives such as N-n-butyl methacrylamide; vinyl chloride, acrylonitrile, styrene, vinyl acetate, etc. However, the hydrophobic monomer to be usable in the present invention is not restricted to these specific examples.
(Hydrophilic Block)

On the other hand, specific examples of the hydrophilic block to be combined with (or bonded to) the above-mentioned block having a cloud point may include: methyl cellulose, dextran, polyethylene oxide, polyvinyl alcohol, poly N-vinyl pyrrolidine, polyvinyl pyridine, polyacrylamide, polymethacrylamide, poly N-methyl acrylamide, polyhydroxymethyl acrylate, polyacrylic acid, polymethacrylic acid, polyvinyl sulfonic acid, polystyrene sulfonic acid, and salts of these acids; poly N,N-dimethylaminoethyl methacrylate, poly N,N-diethylaminoethyl methacrylate, poly N,N-dimethylaminopropyl acrylamide, and salts of these, etc.

The process for combining the above block having a cloud point with the hydrophilic block is not particularly limited. For example, it is preferred to obtain a block copolymer, or a graft copolymer, or a dendrimer-type copolymer containing these blocks.

It is also possible to conduct such a combination by introducing a polymerizable functional group (such as acryloyl group) into either one of the above blocks, and copolymerizing with the resultant product a monomer capable of providing the other block.

Alternatively, it is also possible to obtain a combination product of the above block having a cloud point with the hydrophilic block by copolymerizing a monomer capable of providing the block having a cloud point with a monomer capable of providing the hydrophilic block.

In addition, the block having a cloud point and the hydrophilic block may also be combined or bonded with each other by preliminarily introducing reactive functional groups (such as hydroxyl group, amino group, carboxyl group, and isocyanate group) into both kinds of the blocks, and combining these blocks by using a chemical reaction. At this time, it is usual to introduce a plurality of reactive functional groups into the hydrophilic block.

Further, the polypropylene oxide having a cloud point and the hydrophilic block may be combined or bonded with each other by repetitively subjecting polypropylene oxide and a monomer constituting the above "other water-soluble block" (such as ethylene oxide) to a stepwise or consecutive polymerization, to thereby obtain a block copolymer comprising polypropylene oxide and a water-soluble block (such as polyethylene oxide) combined therewith.

Such a block copolymer may also be obtained by introducing a polymerizable group (such as acryloyl group) into the terminal of polypropylene oxide, and then copolymerizing therewith a monomer constituting the hydrophilic block.

Further, a polymer usable in the present invention may be obtained by introducing a functional group which is reactive in a bond-forming reaction with the terminal functional group of polypropylene oxide (such as hydroxyl group) into a hydrophilic block, and reacting the resultant hydrophilic block and the polypropylene oxide. In addition, a hydrogel-forming polymer usable in the present invention may be obtained by connecting materials such as one comprising polypropylene glycol and polyethylene glycol bonded to both terminals thereof (such as Pluronic F-127; trade name, mfd. by Asahi Denka Kogyo K. K.).

In an embodiment of the present invention wherein the hydrogel-forming polymer comprises a block having a cloud point, at a temperature lower than the cloud point, the polymer may completely be dissolved in water so as to assume a sol state, since the above-mentioned "block having a cloud point" present in the polymer molecule is water-soluble together with the hydrophilic block. However, when a solution of the above polymer is heated up to a temperature higher than the cloud point, the "block having a cloud point" present in the polymer molecule becomes hydrophobic so that separate molecules of the polymer are associated or aggregated with each other due to a hydrophobic interaction.

On the other hand, the hydrophilic block is water-soluble even at this time (i.e., even when heated up to a temperature higher than the cloud point), and therefore, the polymer according to the present invention in water is formed into a hydrogel having a three-dimensional network structure wherein hydrophobic association portions between the blocks having a cloud point constitute the crosslinking points. The resultant hydrogel is again cooled to a temperature lower than the cloud point of the "block having a cloud point" present in the polymer molecule, the block having a cloud point becomes water-soluble and the above crosslinking points due to the hydrophobic association are released or liberated so that the hydrogel structure disappears, whereby the polymer according to the present invention is again formed into a complete aqueous solution. In the above-described manner, the sol-gel transition in the polymer according to the present invention is based on the reversible hydrophilic-hydrophobic conversion in the block having a cloud point present in the polymer molecule at the cloud point, and therefore the transition has a complete reversibility in accordance with a temperature change.
(Solubility of Gel)

As described above, the hydrogel-forming polymer according to the present invention comprising at least a polymer having a sol-gel transition temperature in an aqueous solution thereof, substantially shows a water insolubility at a temperature (d° C.) higher than the sol-gel transition temperature, and reversibly shows water solubility at a temperature (e° C.) lower than the sol-gel transition temperature.

The above-mentioned temperature (d° C.) may preferably be a temperature which is at least 1° C., more preferably at least 2° C. (particularly preferably, at least 5° C.) higher than the sol-gel transition temperature. Further, the above-mentioned "substantial water insolubility" may preferably be a state wherein the amount of the above polymer to be dissolved in 100 ml of water at the above temperature (d° C.) is 5.0 g or less (more preferably 0.5 g or less, particularly preferably 0.1 g or less).

On the other hand, the above-mentioned temperature (e° C.) may preferably be a temperature which is at least 1° C., more preferably at least 2° C. (particularly preferably, at least 5° C.) lower than the sol-gel transition temperature, in terms of the absolute values of these temperatures. Further, the above-mentioned "water solubility" may preferably be a state wherein the amount of the above polymer to be dissolved in 100 ml of water at the above temperature (e° C.) is 0.5 g or more (more preferably 1.0 g or more). The above "to show a reversible water solubility" refers to a state wherein an aqueous solution of the above hydrogel-forming polymer shows the above-mentioned water solubility at a temperature lower than the sol-gel transition temperature, even after the polymer is once formed into a gel state (at a temperature higher than the sol-gel transition temperature).

A 10%-aqueous solution of the above polymer may preferably show a viscosity of 10–3,000 Pa·s (10–3,000 centipoises), more preferably, 50–1,000 Pa·s (50–1,000 centipoises) at 5° C. Such a viscosity may preferably be measured, e.g., under the following measurement conditions:

Viscometer: Stress-controlled type rheometer (model: CSL-500, mfd. by Carri-Med Co., USA)
　Rotor diameter: 60 mm
　Rotor configuration: Parallel-plate type
　Measurement frequency: 1 Hz (hertz)

Even when the an aqueous solution of the hydrogel-forming polymer according to the present invention is formed into a gel state at a temperature higher than the sol-gel transition temperature, and thereafter the resultant gel is immersed in a large amount of water, the gel is not substantially dissolved in water. For example, such a characteristic of the above carrier may be confirmed in the following manner.

More specifically, 0.15 g of the hydrogel-forming polymer according to the present invention is dissolved in 1.35 g of distilled water at a temperature lower than the above sol-gel transition temperature (e.g., under cooling with ice) to thereby prepare a 10 mass %-aqueous solution. Then, the resultant solution is poured into a plastic Petri dish having a diameter of 35 mm, then the dish is warmed up to a temperature of 37° C. to form a gel having a thickness of about 1.5 mm in the dish, and the total weight of the Petri dish (f gram) containing the gel is measured. Then, the entirety of the Petri dish containing the gel is left standing in 250 ml of water at 37° C. for 10 hours, and thereafter the total weight of the Petri dish (g gram) containing the gel is measured, to thereby determine whether the gel has been dissolved from the gel surface or not. At this time, in the hydrogel-forming polymer according to the present invention, the ratio of weight decrease in the gel, i.e., the value of $\{(f-g)/f\}$ may preferably be 5.0% or less, more preferably 1.0% or less (particularly preferably 0.1% or less).

Even when an aqueous solution of the hydrogel-forming polymer according to the present invention was converted into a gel state at a temperature higher than the sol-gel transition temperature, and then the resultant gel was immersed in a large amount (about 0.1–100 times larger than the gel, by volume ratio), the gel was not dissolved for a long period of time. Such a property of the polymer to be used in the present invention may be achieved, e.g., by the presence of at least two (a plurality of) blocks having a cloud point in the polymer molecule.

On the contrary, according to the present inventors' experiments, in a case where a similar gel was formed by using the above-mentioned Pluronic F-127 comprising polypropylene oxide and polyethylene oxide bonded to both terminals thereof, the resultant gel was completely dissolved when the gel is left standing in water for several hours.

In order to suppress the cytotoxicity of a non-gel state to a low level as completely as possible, it is preferred to use a hydrogel-forming polymer which can be converted into a gel state at a concentration of 20% or less (more preferably 15% or less, particularly 10% or less) in terms of the concentration of the polymer based on water, i.e., $\{(polymer)/(polymer+water)\} \times 100(\%)$.

(Other Components)

The carrier according to the present invention comprises at least the above-mentioned polymer having a sol-gel transition temperature. However, the carrier may also comprise another component, as desired. Specific examples of "other components" in such an embodiment may include: antibiotics, anticancer or antitumor substances, ECM such as collagen and gelatin, local chemical mediators appearing hereinafter, hormones such as insulin and growth factors, foreign genes, etc.; and other cells or tissues capable of secreting these chemical mediators and cell growth factors, etc.

The use amount of such "other components" is not particularly limited, as long as it exhibits an intended effect and can be retained in the gel based on the hydrogel-forming polymer for a certain period of time (e.g., for a period necessary for culturing cells or tissue). In general, the amount of the other component to be used may preferably be 2 parts or less, and more preferably 1 part or less, based on the total parts (10 parts) of the hydrogel-forming polymer.

(Chemical Mediator)

There are some cases where the regeneration of a living organism tissue requires not only cells such as precursor cells but also various chemical mediators such as cell growth factor which promotes the differentiation or the growth of the cells. The chemical mediator is generally secreted from cells. However, in order to efficiently conduct the regeneration, it is effective to previously add such a chemical mediator to the cell or tissue-culturing carrier according to the present invention, so as to supply the chemical mediator from the outside of the living organism tissue.

Examples of the above-mentioned chemical mediator may include: 1) local chemical mediators which can act extremely in the vicinity of the cell; 2) neurotransmitters which are secreted by nerve cells and have a extremely short effective acting distance; 3) hormones which are secreted by endocrine cells and systemically act on target cells through bloodstream, etc.; and the like.

Examples of 1) local chemical mediator as described above may include: proteins such as nerve cell growth factors, peptides such as chemotaxis factors, amino acid derivatives such as histamine, fatty acid derivatives such as prostaglandins, etc.

Examples of 2) neurotransmitter as described above may include: low-molecular weight substances including amino acids such as glycine, low-molecular peptides such as noradrenaline, acetylcholine, and enkephalin, etc.

Examples of 3) cell growth factor or hormones as described above may include: cell growth factors such as fibroblast growth factor (FGF), epithelial growth factor (EGF), vascular endothelial growth factor (VEGF) and hapatocyte growth factor (HGF); proteins such as insulin, somatotropin, somatomedin, adrenocorticotropic hormone (ACTH), parathyroid hormone (PTH), and thyroid-stimulating hormone (TSH); glycoproteins, amino acid derivatives such as somatostatin, vasopressin, TSH releasing factor; steroids such as cortisol, estradiol, testosteron; etc.

(Diffusion of Chemical Mediator in Gel)

In the hydrogel according to the present invention, it is possible to arbitrarily control the diffusion rate of a chemical mediator in the hydrogel. Especially, a hydrophilic substance and a hydrophobic substance can be diffused at different diffusion rates. The diffusion of a water-soluble hydrophilic substance is controlled by the molecular sieving effect of the three-dimensional network structure of the hydrogel-forming polymer. Accordingly, in order to reduce the diffusion rate of the water-soluble hydrophilic substance, the concentration of the hydrogel-forming polymer constituting the hydrogel may be increased. Further, the diffusion of the water-soluble hydrophilic substance also is dependent on the molecular weight of the substance. When the concentration of the hydrogel-forming polymer constituting the hydrogel is constant, as the molecular weight of a substance is increased, the diffusion rate thereof becomes lower.

The diffusion of a water-soluble hydrophobic substance in the hydrogel according to the present invention is influenced not only by the molecular sieving effect of the three-dimensional network structure of the hydrogel-forming polymer, but also by the distribution or partition thereof with respect to the hydrophobic portion of the hydrogel-forming polymer. Thus, the diffusion of the water-soluble hydrophobic substance is also controlled by the ratio of the hydrophobic portion in the hydrogel-forming polymer, and therefore, the diffusion of the water-soluble hydrophobic substance is generally slower than that of the water-soluble hydrophilic substance.

The diffusion coefficient of a solute in the hydrogel can be obtained by the "early-time" approximation described in a publication (Eric K. L. Lee et al., Journal of Membrane Science, 24, 125–143 (1985)). In this method, a process in which a solute uniformly diffused on a hydrogel flat plate having a uniform thickness of L (cm) is eluted from both of the surfaces of the hydrogel flat plate is observed along with the elapse of time. When the elution amount of the solute at a time "t" (sec) is represented as Mt, and the elution amount after an infinite time passed is represented by $M_\infty$, the relationship represented by the following formula (1) is satisfied, with respect to a diffusion coefficient D ($cm^2$/sec) of the solute in the hydrogel within the range of $M_t/M_\infty < 0.6$:

$$M_t/M_\infty = (Dt/\pi)^{1/2} \times 4/L \qquad (1)$$

Accordingly, the diffusion coefficient D can be calculated from the gradient of a straight line obtained by plotting the elution rate to the elapsed time t versus the square root of the elapsed time t.

In view of balance between the retention/diffusion (or release) performances with respect to various substances, the ratio of diffusion coefficients of phenol red (PR), methyl blue (MB) and myoglobin (MG) may preferably be such that $(D_{PR}/D_{MB}) \geq 2$ and $(D_{PR}/D_{MG}) \geq 1.2$ in the cell or tissue-culturing carrier according to the present invention. The more preferred ranges of the values are as follows:

(1) $(D_{PR}/D_{MB})$: more preferably 10 or more, further more preferably 20 or more and particularly preferably 50 or more, and preferably $1 \times 10^5$ or less, more preferably $1 \times 10^4$ or less and further more preferably $1 \times 10^3$ or less (2) $(D_{PR}/D_{MG})$: more preferably 1.5 or more, further more preferably 3 or more and particularly preferably 5 or more, and preferably $1 \times 10^4$ or less, more preferably $1 \times 10^3$ or less and further more preferably $1 \times 10^2$ or less.

(Case of Collagen, etc.)

As stated above, collagen, as the conventional cell or tissue-culturing carrier, is a hydrophilic polymer. Unlike in the case of the hydrogel according to the present invention, a balance of hydrophilicity/hydrophobicity in collagen cannot be arbitrarily controlled. Accordingly, it has been difficult to control the diffusion rate of a chemical mediator in collagen.

In the case of polylactic acid or polyglycolic acid, since these polymers have a strong hydrophobicity, it has also been difficult to control the diffusion rate of a chemical mediator in these polymers.

In contrast, since the hydrogel according to the present invention can substantially arbitrarily control a balance of hydrophilicity/hydrophobicity as stated above, it is possible to control the diffusion rate of a chemical mediator in the gel according to the present invention so as to provide a considerable degree of freedom.

When the gel according to the present invention is used in combination with a known gel-forming polymer such as collagen (that is, when the polymer according to the present invention and a known gel-forming polymer such as collagen are co-present as gel-forming polymers), it is also possible to control the diffusion rate of a chemical mediator so as to provide a considerable degree of freedom, even in the gel also containing a known gel-forming polymer such as collagen.

(Tissue or Organ in Living Body)

The term "a cell or tissue" is used in the present invention to mean tissues, apparatuses or organs which are present in the living bodies of animals (especially humans). The in vivo tissue or organ which can be regenerated by using the carrier according to the present invention is not particularly limited. Examples of such tissue or organ may include: esophagus, stomach, small intestine, large intestine, pancreas, liver, heart, blood vessel, bone, cartilage, nerve, cornea, corium, etc.

(Cell or Tissue)

The cells or tissue which can be cultured by using culturing carrier according to the present invention is not particularly limited.

The culturing carrier according to the present invention can be used particularly effectively for differential cells or tissues. Examples of such differential cells may include stem cells and precursor cells. The differential cells include any of differential unipotent cells, differential pluripotent cells, and differential totipotent cells.

(Method of Repairing or Regenerating Living Organism Tissue or Organ)

The method of repairing or regenerating a cell or tissue using the carrier according to the present invention is not particularly limited. From the viewpoint of easy inoculation and recovery of cells or the like, it is preferable to utilize the sol-gel transition of a hydrogel-forming polymer.

(Embodiment of Using Sol-Gel Transition)

In an embodiment of using such sol-gel transition, a cell (e.g., a stem cell or precursor cell), tissue containing the cell, or the like is first inoculated or mixed into the carrier according to the present invention. In order to carry out such inoculation or mixing, for example, a hydrogel-forming polymer constituting the carrier used for culturing a cell or tissue of the present invention is dissolved in a culture medium such as RPMI-1640 (Life Technologies, N.Y., USA) at a low temperature (e.g., 4° C.) while stirring, so that the carrier according to the present invention is converted into a state of an aqueous solution (a sol state) with a temperature lower than its sol-gel transition temperature, and then the above cell or tissue may be added or suspended therein. A culture medium used herein is not particularly limited. A culture medium in which a cell of interest (a stem cell, a precursor cell, etc.) easily grows or differentiates may be appropriately selected and used. In addition, the above described chemical mediator promoting the growth or differentiation of a stem cell or precursor cell of interest may also be added to such a culture medium, as desired. Moreover, ECM such as collagen or gelatin may also be added thereto.

In order to regenerate a living organism tissue or organ in the carrier according to the present invention, for example, the above suspension is heated to a temperature (usually 37° C.) higher than the sol-gel transition temperature of the carrier according to the present invention, so that it is gelatinized. Thereafter, a cell of interest or tissue containing the cell may be cultured at the temperature (usually 37° C.).

When the carrier according to the present invention is gelatinized, it is also possible to gelatinize it in a desired form, using a mold having the desired form. For example, when a cartilage tissue is used in repair of the ear or nose, the carrier according to the present invention is converted into a form compatible with a portion of the ear or nose to which the cartilage tissue is to be applied. Thereafter, cartilage cells are cultured in the carrier according to the present invention, so as to regenerate a cartilage tissue. Thus, the cartilage tissue to be applied can be easily molded into a desired form and used.

In order to recover a tissue or organ of interest from the carrier according to the present invention after the tissue or organ is regenerated therein, the carrier according to the present invention containing the tissue or organ of interest is cooled to a temperature (for example, 4° C.) lower than the sol-gel transition temperature, so that the carrier according to the present invention is returned to a sol state. Thereafter, the tissue or organ of interest may be separated from the carrier according to the present invention by a common separation method such as centrifugal separation.

As stated above, it is possible for the carrier according to the present invention substantially not to inhibit (or substantially to promote) the growth or differentiation of a cell of interest (a stem cell, a precursor cell, etc.), while controlling the growth of fibroblasts. Accordingly, a cell or organ of interest can be efficiently regenerated in the carrier according to the present invention.

EXAMPLES

Hereinbelow, the present invention will be described in more detail with reference to Examples. However, it should be noted that the present invention is defined by Claims, but is not limited by the following Examples.

Production Example 1

10 g of a polypropylene oxide-polyethylene oxide copolymer (average polymerization degree of propylene oxide/ethylene oxide=about 60, Pluronic F-127, mfd. by Asahi Denka K. K.) was dissolved in 30 ml of dry chloroform, and in the co-presence of phosphorus pentaoxide, 0.13 g of hexamethylene diisocyanate was added thereto, and the resultant mixture was subjected to reaction under refluxing at the boiling point for six hours. The solvent was distilled off unde reduced pressure, the resultant residue was dissolved in distilled water, and subjected to ultrafiltration by using an ultrafiltration membrane having a molecular cutoff of $3 \times 10^4$ (Amicon PM-30) so as to fractionate the product into a low-molecular weight polymer fraction and a high-molecular weight polymer fraction. The resultant aqueous solution was frozen, to thereby obtain a high-polymerization degree product of F-127 and a low-polymerization degree product of F-127.

When the above high-polymerization degree product of F-127 (TGP-1, a hydrogel-forming polymer according to the present invention) was dissolved in distilled water under ice-cooling in an amount of 8 mass %. When the resultant aqueous solution was gradually warmed, it was found that the viscosity was gradually increased from 21° C., and was solidified at about 27° C. so as to be converted into a hydrogel state. When the resultant hydrogel was cooled, it was returned to an aqueous solution at 21° C. Such a conversion was reversibly and repetitively observed. On the other hand, a solution which had been obtained by dissolving the above low-polymerization degree product of F-127 in distilled water under ice-cooling in an amount of 8 mass %, was not converted into a gel state at all even when it was heated to 60° C. or higher.

Production Example 2

160 mol of ethylene oxide was subjected to an addition reaction with 1 mol of trimethylol propane by cationic polymerization, to thereby obtain polyethylene oxide triol having an average molecular weight of about 7000.

100 g of the thus obtained polyethyleneoxide triol was dissolved in 1000 ml of distilled water, and then 12 g of potassium permanganate was slowly added thereto at room temperature, and the resultant mixture was subjected to an oxidization reaction at this temperature for about one hour. The resultant solid content was removed by filtration, and the product was subjected to extraction with chloroform, and the solvent (chloroform) was distilled off, to thereby obtain 90 g of a polyethylene oxide tricarboxyl derivative.

10 g of the thus obtained polyethylene oxide tricarboxyl derivative, and 10 g of polypropylene oxide diamino derivative (average propylene oxide polymerization degree: about 65, trade name: Jeffamine D-4000, mfd. by Jefferson Chemical Co., U.S.A., cloud point: about 9° C.) were dissolved in 1000 ml of carbon tetrachloride, and then 1.2 g of dicyclohexyl carbodiimide was added thereto, and the resultant mixture was allowed to cause a reaction for 6 hours under refluxing at boiling point. The resultant reaction mixture was cooled and the solid content was removed by filtration, and thereafter the solvent (carbon tetrachloride) therein was distilled off under reduced pressure. Then, the resultant residue was dried under vacuum, to thereby obtain a polymer for coating (TGP-2) comprising plural polypropylene oxide blocks, and polyethylene oxide block combined therewith. This polymer was dissolved in distilled water under cooling with ice so as to provide a concentration of 5 mass %. When the sol-gel transition temperature of the resultant aqueous solution was measured, it was found that the sol-gel transition temperature was about 16° C.

Production Example 3

96 g of N-isopropyl acrylamide (mfd. by Eastman Kodak Co.), 17 g of N-aclyloxy succinimide (mfd. by Kokusan Kagaku K. K.), and 7 g of n-butyl methacrylate (mfd. by Kanto Kagaku K. K.) were dissolved in 4000 ml of chloroform. After the purging with nitrogen gas, 1.5 g of N,N'-azobisisobutyronitrile was added thereto, and the resultant mixture was subjected to polymerization at 60° C. for 6 hours. The reaction mixture was concentrated, and then was reprecipitated in diethyl ether. The resultant solid content was recovered by filtration, and then was dried under vacuum, to thereby obtain 78 g of poly (N-isopropyl acrylamide-co-N-aclyloxy succinimide-co-n-butyl methacrylate).

Then, an excess of isopropylamine was added to the thus obtained poly(N-isopropyl acrylamide-co-N-aclyloxy succinimide-co-n-butyl methacrylate) to thereby obtain poly (N-isopropyl acrylamide-co-n-butyl methacrylate). The thus obtained poly(N-isopropyl acrylamide-co-n-butyl methacrylate) had a sol-gel transition temperature of about 19° C. in its aqueous solution.

Then, 10 g of the thus obtained poly(N-isopropyl acrylamide-co-N-aclyloxy succinimide-co-n-butyl methacrylate) and 5 g of both terminal-aminated polyethylene oxide (molecular weight=6000, mfd. by Kawaken Fine Chemical K.K.) were dissolved in 1000 ml of chloroform, and the resultant mixture was allowed to cause a reaction at 50° C. for 3 hours. The reaction mixture was cooled to room temperature, and thereafter 1 g of isopropylamine was added thereto, and was left standing for 1 hour. The reaction mixture was concentrated, and then was precipitated in diethyl ether. The solid content was recovered by filtration, and thereafter was dried under vacuum, to thereby obtain a polymer for coating (TGP-3) comprising plural poly(N- isopropyl acrylamide-co-n-butyl methacrylate) blocks and polyethylene oxide block combined therewith.

This polymer was dissolved in distilled water under cooling with ice so as to provide a concentration of 5 mass %. When the sol-gel transition temperature of the resultant aqueous solution was measured, it was found that the sol-gel transition temperature was about 21° C.

Production Example 4

(Sterilization Method)

2.0 g of the above-mentioned polymer (TGP-1) was placed in an EOG (ethylene oxide gas) sterilizing bag (trade name: Hybrid Sterilization bag, mfd. by Hogi Medical Co.), and was filled up with EOG by use of an EOG sterilizing device (trade name: Easy Pack, mfd. Inouchi Seieido Co.) and then the bag was left standing at room temperature for twenty-four hours. Further, the bag was left standing at 40° C. for half a day, EOG was removed from the bag and the bag was subjected to aeration. The bag was placed in a vacuum drying chamber (40° C.) and was left standing for half a day, and was sterilized while the bag was sometimes subjected to aeration.

Separately, it was confirmed that the sol-gel transition temperature of the polymer was not changed even after this sterilization operation.

Production Example 5

37 g of N-isopropylacrylamide, 3 g of n-butyl methacrylate, and 28 g of polyethylene oxide monoacrylate (having a molecular weight of 4,000, PME-4000 mfd. by Nihon Yushi K.K. (NOF Corporation)) were dissolved in 340 mL of benzene. Thereafter, 0.8 g of 2,2'-azobisisobutyronitrile was added to the resultant solution, and then was subjected to a reaction at 60° C. for 6 hours. 600 mL of chloroform was added to the thus obtained reaction product so as to be dissolved therein and the resultant solution was dropped into 20 L (liter) of ether so as to be precipitated therein. The resultant precipitate was recovered by filtration, and the precipitate was then subjected to vacuum drying at about 40° C. for 24 hours. Thereafter, the resultant product was again dissolved in 6 L of distilled water. The solution was concentrated to a volume of 2 L at 10° C. by using a hollow fiber ultrafiltration membrane with a molecular weight cutoff of $10 \times 10^4$ (HIP100-43 mfd. by Amicon),.

The concentrated solution was diluted with 4 L of distilled water, and then, the dilution operation was carried out again. The above dilution and concentration by ultrafiltration were further repeated 5 times, so as to eliminate products having a molecular weight of $10 \times 10^4$ or lower. The product which had not been filtrated by this ultrafiltration (i.e., the product remaining in the inside of the ultrafiltration membrane) was recovered and freeze-dried, so as to obtain 60 g of a hydrogel-forming polymer (TGP-4) according to the present invention having a molecular weight of $10 \times 10^4$ or higher.

1 g of the thus obtained hydrogel-forming polymer (TGP-4) according to the present invention was dissolved in 9 g of distilled water under ice cooling. When the sol-gel transition temperature of the obtained aqueous solution was measured, it was found to be 25° C.

Production Example 6

The hydrogel-forming polymer (TGP-3) according to the present invention which had been obtained in Production Example 3 was dissolved so as to provide a concentration of 10 mass % in distilled water. When the steady flow viscosity η thereof at 37° C. was measured, it was found to be $5.8 \times 10^5$ Pa·sec. In the measurement of the steady flow viscosity η, a stress rheometer (CSL 500), and an acryl disk (diameter: 4 cm) as a measuring device were used. The thickness of a sample was set to 600 μm, and applying a shearing stress of 10 N m$^2$, the resultant creep was measured for 5 minutes after 5 minutes had passed.

On the other hand, agar was dissolved so as to provide a concentration of 2 mass % in distilled water at 90° C., and the mixed solution was converted into a gel state at 10° C. for 1 hour. Thereafter, η thereof at 37° C. was measured. As a result, the obtained value exceeded the measurement limit ($1 \times 10^7$ Pa·sec) of the apparatus.

Production Example 7

(Evaluation of the Growing Property of Fibroblasts)

The hydrogel-forming polymer (TGP-3) according to the present invention which had been obtained in Production Example 3 was sterilized by the method which had been used in Production Example 4. Thereafter, the sterilized polymer was dissolved under stirring in RPMI-1640 (mfd. by Life Technologies) containing 20% fetal calf serum (FCS; mfd. by Dainippon Pharmaceutical; trade name: Fetal Calf Serum) and an antibiotic (mfd. by Life Technologies; trade name; penicillin; final concentration: 10,000 U/mL) at 4° C. for 24 hours, so as to provide a final concentration of the polymer of about 8%. This operation was carried out aseptically.

Normal human lung fibroblasts (NHLF, mfd. by Takara Shuzo Co., Ltd.) were dispersed in the above carrier (TGP-3/RPMI) according to the present invention, so as to provide a cell density of $6 \times 10^4$ cells/mL. 0.2 mL each of this NHLF dispersion was poured into each well of a 24-well plate [flat bottom multi-well tissue culture plate (FALCON, Becton Dickinson & Company)], and then was converted into a gel state at 37° C. Thereafter, 0.4 mL of culture solution was added thereto, and then was subjected to culturing at 37° C. under 5% $CO_2$, atmospheric pressure. Two 24-well plates were prepared for the observation with a microscope and for measurement of the growth rate of fibroblasts. In order to conduct the observation with the elapse of time on the 0th, 1st, 3rd and 7th days following the day of culture, eight 24-well plates were prepared in total.

Separately, without using TGP-3, NHLF was dispersed in the above culture solution, so as to provide a cell density of $6 \times 10^4$ cells/mL. Thus, an NHLF dispersion was prepared as a control. Thereafter, eight 24-well plates were prepared in the same manner as described above, and they were subjected to the same culture test.

The observation was carried out with the elapse of time (on the 0th, 1st, 3rd and 7th days following the day of culture), by using a phase-contrast microscope (mfd. by Olympus Corporation; trade name: IMT-2; magnification: 10 times). As a result, in the case of the culturing of the control (RPMI), characteristic arborescent the growth of fibroblasts was observed after 1 day had passed, and it reached a confluent state after 7 days had passed. In contrast, in the case of the culturing of the carrier (TGP-3/RPMI) according to the present invention, fibroblasts remained in a unicellular state even after 7 days had passed, and no the growth of the cells was observed.

After predetermined culturing days had passed, the temperature of the 24-well plate was decreased to 4° C. to dissolve the carrier. Thereafter, 50 μl of a WST-8 reagent (Dojindo Laboratories) as a reagent for determining the activity of succinate dehydrogenase was added to each well.

The thus prepared 24-well plate was subjected to a reaction at 4° C. for 10 hours, and then a completely homogenous aqueous solution was prepared.

200 µl each of the above aqueous solution was poured into each well of a 96-well plate. The absorbance (OD (450)) was measured at 450 nm (reference wavelength: 620 nm) by using a chromatometer for microplates. The growth rate of fibroblasts was obtained as a ratio ($OD_L/OD_f$) between the absorbance at the beginning of the culture (on the 0th day) $OD_f$=(OD (450)) and the absorbance after the culture (after 1, 3 and 7 days passed) $OD_L$=(OD (450)).

In the carrier (TGP-3/RPMI) according to the present invention, the growth rates ($OD_L/OD_f$) of fibroblasts were 105%, 120% and 125%, respectively, when 1, 3 and 7 days had passed after the culture. In contrast, in the case of the control (RPMI), the growth rates ($OD_L/OD_f$) of fibroblasts were 170%, 370% and 420%, respectively, when 1, 3 and 7 days had passed after the culture.

Example 1

A beagle-mixed dog (with a body weight of 9.0 to 11.0 kg) was anesthetized by intravenous injection of pentobarbital, and then underwent laparotomy, and the pancreas as a whole was removed. A guide wire with a diameter of 100 µm was inserted into the pancreatic duct, and pancreatic tissues were cut along the guide wire and removed. Thus, only the pancreatic duct could be collected. The pancreatic duct having a length of approximately 6 cm and a diameter of 150 to 200 µm was sliced to 0.5 mm width slices.

The hydrogel-forming polymer (TGP-3) of the present invention obtained in Production Example 3 was dissolved in a concentration of 10% by mass in a culture medium (RPMI-1640, manufactured by Life Technologies), so as to prepare a solution (the carrier of the present invention). The obtained solution was cooled to 4° C., and the above pancreatic duct slices were dispersed therein. 0.4 ml each of the thus obtained solution was then poured into each well of a 12-well plate [flat bottom multiwell tissue culture plate (FALCON, Becton Dickinson & Company)], followed by gelatinization at 37° C. Thereafter, 0.4 ml of culture medium was added thereto, and the mixture was cultured at 37° C. under 5% $CO_2$ atmospheric pressure. It is noted that the culture medium RPMI-1640 contained 10% canine serum (obtained by collecting 50 to 100 ml of blood from a dog, leaving it at rest at room temperature for 30 minutes, and then collecting the supernatant), 10 mM nicotinamide (manufactured by Sigma, product name: NIACINAMIDE), and a 10 ng/ml keratinocyte growth factor (KGF; manufactured by PEPROTECH FC Ltd., product name: Recombinant Keratinocyte Growth Factor).

Figure 2:
FIG. 2 is a photomicrograph showing a mass of cells which has been enlarged with the elapse of time in Example 1 (on the $30^{th}$ day after the day of culture, magnification: ×100).

When the culture product was observed over time, using a stereoscopic microscope (manufactured by Olympus, product name: Inverted System Microscope, magnification: 100 times), an agglomeration obtained by differentiation and growth of cells was recognized at the outside of a piece of pancreatic duct tissues on the $5^{th}$ day of culture (FIG. 1). This mass of cells enlarged over time, and it became 150 µM on the $14^{th}$ day, and 300 µm on the $30^{th}$ day (FIG. 2). In a tissue image on the $30^{th}$ day, insulin-positive cells existed in the cell mass, and thus, it was indicated that a cluster called an islet of Langerhans was formed.

The carrier of the present invention containing the cell mass was cooled to 4° C., followed by centrifugal separation, so that the cell mass could be easily separated from the carrier of the present invention that was solated by the cooling.

Example 2

The costal cartilage was aseptically removed from a 4-week-old Lewis rat, and soft tissues attached thereto were eliminated. The thus obtained cartilage was then sliced. Thereafter, each of enzyme solutions {the first solution: 0.1% EDTA (manufactured by Nacalai Tesque, Inc.)/PBS (−) (manufactured by Roman Industries, Co., Ltd.); the second solution: 0.25% trypsin-EDTA (manufactured by Gibco)/PBS (−) (manufactured by Roman Industries, Co., Ltd.); and the third solution: 0.1% collagenase (Wako Pure Chemical Industries, Ltd.)/PBS(+) (manufactured by Gibco)} was placed in a test tube. The above cartilage tissue was then placed in the test tube, and it was then treated at 37° C. for 15 minutes, 1 hour and 3 hours, respectively, so as to decompose the above cartilage tissue.

The collected cartilage dispersed solution was added into a medium {D-MEM (Dulbecco's Modified Eagle Medium (manufactured by Gibco))+10% FCS (Fetal Bovine Serum)+penicillin+streptomycin}, and the mixture was cultured for about 2 weeks at 37° C. under 5% $CO_2$ atmospheric pressure, so that it was cultured to a confluent state. The obtained culture medium was treated with 0.25% trypsin/PBS(−) for 5 minutes, and then subjected to centrifugal separation at 1,000 rpm for 10 minutes, so as to recover cartilage cells.

The hydrogel-forming polymer (TGP-3) of the present invention obtained in Production Example 3 was dissolved in a concentration of 10% by mass in a culture medium (RPMI-1640, manufactured by Life Technologies), so as to prepare a solution (the carrier of the present invention). The obtained solution was cooled to 4° C., and the above cartilage cells were dispersed therein so that the cell density was set to 6×10⁵ cells/ml. 0.4 ml each of the thus obtained solution was then poured into each well of a 12-well plate [flat bottom multiwell tissue culture plate (FALCON, Becton Dickinson & Company)], followed by gelatinization at 37° C. Thereafter, 0.4 ml of culture medium was added thereto, and the mixture was cultured at 37° C. under 5% $CO_2$ atmospheric pressure. It is noted that 10% rat serum (obtained by leaving rat blood at rest at room temperature for 30 minutes, and then collecting the supernatant), 10 mM nicotinamide, and a 10 ng/ml keratinocyte growth factor (KGF) was added to the culture medium RPMI-1640 in the same manner as in Example 1.

When the culture product was observed over time, using a stereoscopic microscope, an agglomeration obtained by differentiation and growth of cells was recognized on the $5^{th}$ day after the day of culture. This mass of cells enlarged over time, and it became 150 µM on the $14^{th}$ day, and then 300 µm on the $30^{th}$ day. In a tissue image on the $30^{th}$ day (obtained by Azan staining and Aggrecan immunostaining), a stained image showing the formation of a mass of cartilage was recognized in the cell mass.

The carrier of the present invention containing the cell mass was cooled to 4° C., followed by centrifugal separation, so that the cell mass could be easily separated from the carrier of the present invention that was solated by the cooling.

Production Example 8

71.0 g of N-isopropylacrylamide and 4.4 g of n-butyl methacrylate were dissolved in 1,117 g of ethanol. To the resultant miture solution, an aqueous solution which had been obtained by dissolving 22.6 g of polyethylene glycol dimethacrylate (PDE 6000, mfd. by NOF Corporation) in 773 g of water was added. The oresultant solution was heated to 70° C. under a nitrogen stream. While the solution was maintaining at 70° C. under a nitrogen stream, 0.8 mL of N,N,N',N'-tetramethylethylenediamine (TEMED) and 8 mL of 10% ammonium persulfate (APS) aqueous solution were added to the solution, and then was subjected to a reaction for 30 minutes under stirring. Further, 0.8 mL of TEMED and 8 mL of 10% APS aqueous solution were added thereto 4 times at 30-minute intervals, and the polymerization reaction was terminated. The reaction mixture was cooled to 10° C. or lower, it was diluted with 5 L of cold distilled water with a temperature of 10° C. Thereafter, the solution was concentrated to 2 L at 10° C., by using an ultrafiltration membrane with a molecular weight cutoff of $10 \times 10^4$.

4 L of cold distilled water was added to the concentrated solution for dilution, and the above concentration operation using the ultrafiltration was conducted again. Thereafter, the above dilution and ultrafiltration concentration were repeated 5 times, so as to eliminate products with a molecular weight of $10 \times 10^4$ or lower. The product which had not been filtrated by the above ultrafiltration (product remaining in the ultrafiltration membrane) was recovered and freeze-dried, so as to obtain 72 g of the hydrogel-forming polymer (TGP-5) according to the present invention with a molecular weight of $10 \times 10^4$ or higher.

1 g of the thus obtained hydrogel-forming polymer (TGP-5) according to the present invention was dissolved in 9 g of distilled water under ice cooling. When the sol-gel transition temperature of this aqueous solution was measured, it was found to be 20° C.

Production Example 9

42.0 g of N-isopropylacrylamide and 4.0 g of n-butyl methacrylate were dissolved in 592 g of ethanol. To the resultant mixture solution, an aqueous solution which had been obtained by dissolving 11.5 g of polyethylene glycol dimethacrylate (PDE 6000, mfd. by NOF Corporation) in 65.1 g of water was added. The resultant solution was heated to 70° C. under a nitrogen stream. While the solution was maintained at 70° C. under a nitrogen stream, 0.4 mL of N,N,N',N'-tetramethylethylenediamine (TEMED) and 4 mL of 10% ammonium persulfate (APS) aqueous solution were added to the solution, and then, the thus obtained solution was subjected to a reaction for 30 minutes under stirring. Further, 0.4 mL of TEMED and 4 mL of 10% APS aqueous solution were added thereto 4 times at 30-minute intervals, and the polymerization reaction was terminated. The reaction mixture was cooled to 5° C. or lower, it was diluted with 5 L of cold distilled water with a temperature of 5° C. Thereafter, the solution was concentrated to 2 L at 5° C., by using an ultrafiltration membrane with a molecular weight cutoff of $10 \times 10^4$.

4 L of cold distilled water was added to the concentrated solution for dilution, and the above concentration operation using the ultrafiltration was conducted again. Thereafter, the above dilution and ultrafiltration concentration were repeated 5 times, so as to eliminate The product with a molecular weight of $10 \times 10^4$ or lower. The product which had not been filtrated by the above ultrafiltration (product remaining in the ultrafiltration membrane) was recovered and freeze-dried, so as to obtain 40 g of the hydrogel-forming polymer (TGP-6) according to the present invention with a molecular weight of $10 \times 10^4$ or higher.

1 g of the thus obtained hydrogel-forming polymer (TGP-6) according to the present invention was dissolved in 9 g of distilled water under ice cooling. When the sol-gel transition temperature of this aqueous solution was measured, it was found to be 7° C.

Production Example 10

45.5 g of N-isopropylacrylamide and 0.56 g of n-butyl methacrylate were dissolved in 592 g of ethanol. To the resultant mixture solution, an aqueous solution which had been obtained by dissolving 11.5 g of polyethylene glycol dimethacrylate (PDE 6000, mfd. by NOF Corporation) in 65.1 g of water was added. The resultant solution was heated to 70° C. under a nitrogen stream. While the solution was maintained at 70° C. under a nitrogen stream, 0.4 mL of N,N,N',N'-tetramethylethylenediamine (TEMED) and 4 mL of 10% ammonium persulfate (APS) aqueous solution were added to the solution, and then was subjected to a reaction for 30 minutes under stirring. Further, 0.4 mL of TEMED and 4 mL of 10% APS aqueous solution were added thereto 4 times at 30-minute intervals, and the polymerization reaction was terminated. The reaction mixture was cooled to 10° C. or lower, it was diluted with 5 L of cold distilled water with a temperature of 10° C. Thereafter, the solution was concentrated to 2 L at 10° C., by using an ultrafiltration membrane with a molecular weight cutoff of $10 \times 10^4$.

4 L of cold distilled water was added to the concentrated solution for dilution, and the above concentration operation using the ultrafiltration was conducted again. Thereafter, the above dilution and ultrafiltration concentration were repeated 5 times, so as to eliminate The product with a molecular weight of $10 \times 10^4$ or lower. The product which had not been filtrated by the above ultrafiltration (product remaining in the ultrafiltration membrane) was recovered and freeze-dried, so as to obtain 22 g of the hydrogel-forming polymer (TGP-7) according to the present invention with a molecular weight of $10 \times 10^4$ or higher.

1 g of the thus obtained hydrogel-forming polymer (TGP-7) according to the present invention was dissolved in 9 g of distilled water under ice cooling. When the sol-gel transition temperature of this aqueous solution was measured, it was found to be 37° C.

Example 3

The hydrogel-forming polymer TGP-5 obtained in Production Example 8 was dissolved so as to provide a concentration of 9 wt % under ice cooling, in each of a phosphate buffer solution (1/15 M, pH 7) containing 3 mM phenol red (Wako Pure Chemical Industries, Ltd.), a phosphate buffer solution (1/15 M, pH 7) containing 6 mM methyl blue (Wako Pure Chemical Industries, Ltd.), and a phosphate buffer solution (1/15 M, pH 7) containing 0.9% myoglobin (Wako Pure Chemical Industries, Ltd.). A glass tube having a length of 1.3 mm and an inside diameter of 6 mm was filled with each of the resultant solutions, and then the temperature was increased to 37° C., so that the solution was converted into a gel state. The thus obtained disk-shaped hydrogel together with the glass tube containing the same was placed in a spectroscopic cell containing 3 mL of phosphate buffer solution (1/15 M, pH 7). The temperature was retained at 37° C., and under stirring, the absorbance was sequentially measured. The absorbance of phenol red, methyl blue and myoglobin was measured at measuring wavelengths of 558 nm, 571 nm and 409 nm, respectively. The elution rate of each of phenol red, methyl blue and myoglobin into 3 mL of phosphate buffer solution (1/15 M, pH 7) along with the elapse of time was obtained by measuring the absorbance of these components. When the diffusion coefficients of phenol red, methyl blue and myoglobin were determined according to formula (1), the values were found to be $1.6 \times 10^{-6}$ (cm$^2$/sec), $7.5 \times 10^{-9}$ (cm$^2$/sec), and $2.1 \times 10^{-7}$ (cm$^2$/sec), respectively.

Phenol red was a water-soluble hydrophilic substance and methyl blue is a water-soluble hydrophobic substance. The ratio (DPR/DMB) of the diffusion coefficients of phenol red and methyl blue at 37° C. in the hydrogel TGP-5 was 213.

Phenol red was a water-soluble hydrophilic low molecular weight substance and myoglobin was a water-soluble hydrophilic high molecular weight substance. The ratio ($D_{PR}/D_{MG}$) of the diffusion coefficients of phenol red and myoglobin at 37° C. in the hydrogel TGP-5 was 7.6.

Comparative Example 1

Low melting point agarose (Sea Prep (registered trade mark) agarose mfd. by BMA (Rockland USA); melting point: 50° C. or lower; gel formation point: 8° C. to 17° C.) was dissolved so as to provide a concentration of 1 wt %, while heating, in each of a phosphate buffer solution (1/15 M, pH 7) containing 3 mM phenol red (Wako Pure Chemical Industries, Ltd.), a phosphate buffer solution (1/15 M, pH 7) containing 6 mM methyl blue (Wako Pure Chemical Industries, Ltd.), and a phosphate buffer solution (1/15 M, pH 7) containing 0.9% myoglobin (Wako Pure Chemical Industries, Ltd.). A glass tube having a length of 10 mm and an inside diameter of 2 mm was filled with each of the resultant solutions, and was cooled to 2° C., so that the solution was converted into a gel state. The obtained cylindrical hydrogel together with the glass tube containing the same was placed in a spectroscopic cell containing 3 mL of phosphate buffer solution (1/15 M, pH 7). The temperature was retained at 37° C., and under stirring, the absorbance was sequentially measured. The absorbance of phenol red, methyl blue and myoglobin was measured at measuring wavelengths of 558 nm, 571 nm and 409 nm, respectively. The elution rate of each of phenol red, methyl blue and myoglobin into 3 mL of phosphate buffer solution (1/15 M, pH 7) along with the elapse of time was obtained by measuring the absorbance of these components. When the diffusion coefficients of phenol red, methyl blue and myoglobin were determined according to formula (1), the values were $4.7 \times 10^{-6}$ (cm$^2$/sec), $7.1 \times 10^{-6}$ (cm$^2$/sec), and $2.6 \times 10^{-5}$ (cm$^2$/sec), respectively.

Phenol red was a water-soluble hydrophilic substance and methyl blue is a water-soluble hydrophobic substance. The ratio ($D_{PR}/D_{MG}$) of the diffusion coefficients of phenol red and methyl blue at 37° C. in the low melting point agarose hydrogel was 0.7.

Phenol red was a water-soluble hydrophilic low molecular weight substance, and myoglobin was a water-soluble hydrophilic high molecular weight substance. The ratio ($D_{PR}/D_{MG}$) of the diffusion coefficients of phenol red and myoglobin at 37° C. in the low melting point agarose hydrogel was 0.18.

Example 4

The hydrogel-forming polymers TGP-5 obtained in Production Examples 8 was dissolved in a physiological salt solution, so as to prepare solutions having polymer concentrations of 10 mass % (wt %), 8 mass % (wt %) and 6 mass % (wt %). When the sol-gel transition temperature of each of the resultant solutions was measured, they were 18° C., 20° C. and 22° C., respectively. Each of the physiological salt solutions was cooled to the sol-gel transition temperature thereof or lower. Thereafter, each of the solutions was administered into the abdominal cavity of each of 6-week-old rats in a group comprising 10 rats (5 male rats and 5 female rats) in an amount of 1 mL/kg. The administration method comprises dehairing the abdominal region of a rat with an electric clipper, disinfecting an administration portion with ethanol for disinfection, and administering the above solution therein with a syringe and an indwelling needle (22G). On the 1st, 3rd, 7th, 14th and 21st days after the administration, two rats (one male, one female) from each group were subjected to exsanguination under ether anesthesia, and they were sacrificed. Thereafter, the remaining of hydrogel (carrier according to the present invention) in their abdominal cavity was checked. As a result, the hydrogel with a polymer concentration of 6 mass % (wt %) disappeared from the abdominal cavity on the 3rd day after the administration. The hydrogel with a polymer concentration of 8 mass % (wt %) disappeared from the abdominal cavity on the 14th day after the administration, and the hydrogel with a polymer concentration of 10 mass % (wt %) disappeared from the abdominal cavity on the 21st day after the administration.

Industrial Applicability

As described hereinabove, since fibroblasts exhibit substantially no growth in the carrier for culturing a cell or tissue according to the present invention, the carrier selectively allows a cell or tissue of interest (for example, cells of an organ or tissue to be repaired or regenerated) to grow, thereby effectively achieving the regeneration of an organ or tissue of interest.

The carrier for culturing a cell or tissue of the present invention is formed into a gel state at a predetermined temperature (for example, the body temperature of humans or animals) to form a three-dimensional network structure, so that it can retain a cell growth factor or the like for a long period of time, thereby promoting the regeneration of an organ or tissue of interest.

The carrier for culturing a cell or tissue of the present invention may be constituted by using a hydrogel-forming polymer which assumes a sol state at a low temperature but is formed into a gel state at a body temperature. A stem cell, precursor cell, or tissue containing such a cell can be inoculated or mixed into the carrier according to the present invention in a sol state at a low temperature, and the thus obtained carrier is then formed into a gel state at a predetermined temperature (for example, at the body temperature of humans or animals). Thus, the carrier in a gel state can function as an artificial carrier for adhesion, differentiation or morphogenesis of a stem cell or precursor cell which regenerates a tissue or organ.

Moreover, since the carrier for culturing a cell or tissue according to the present invention is returned to a sol state, when it is cooled to a temperature lower than its sol-gel transition temperature, a tissue or organ which has been generated in the gel can be recovered substantially without imparting a damage thereto.

What is claimed is:

1. A cell or tissue-culturing carrier, comprising, a hydrogel-forming polymer; an aqueous solution of the hydrogel-forming polymer showing a thermo-reversible sol-gel transition such that it assumes a sol state at a lower temperature and assumes a gel state at a higher temperature; and fibroblasts showing substantially no growing property in a gel based on the hydrogel-forming polymer.

2. A cell or tissue-culturing carrier according to claim 1, wherein the hydrogel-forming polymer is a polymer comprising a plurality of blocks having a cloud point, and a hydrophilic block combined therewith.

3. A cell or tissue-culturing carrier according to claim 1 or 2, wherein the sol-gel transition temperature is higher than 0° C. and not higher than 42° C.

4. A cell or tissue-culturing carrier according to claim 1, further comprising a chemical mediator.

5. A cell or tissue-culturing carrier according to claim 1, wherein the aqueous solution of the hydrogel-forming polymer assumes a gel state which is substantially water-insoluble at a high temperature.

6. A cell or tissue-culturing carrier according to claim 1, further comprising water.

7. A cell or tissue-culturing carrier according to claim 1, wherein the ratios of diffusion coefficients of phenol red (PR), methyl blue (MB) and myoglobin (MG) satisfy the relationships of: $(D_{PR}/D_{MB}) \geq 2$ and $(D_{PR}/D^{MG}) \geq 1.2$.

8. A method of culturing a cell or tissue, comprising:

providing a cell or tissue-culturing carrier comprising, a hydrogel-forming polymer; an aqueous solution of the hydrogel-forming polymer showing a thermo-reversible sol-gel transition such that it assumes a sol state at a lower temperature and assumes a gel state at a higher temperature; and fibroblasts showing substantially no growing property in a gel based on the hydrogel-forming polymer;

adding a cell or tissue to the carrier assuming a sol state at a temperature lower than the sol-gel transition temperature thereof culturing the cell or tissue by using the carrier assuming a gel state at a temperature higher than the sol-gel transition temperature thereof; and recovering the cultured cell or tissue by converting again the carrier into a sol state at a temperature lower than the sol-gel transition temperature thereof.

* * * * *